United States Patent [19]
Järvelin et al.

[11] Patent Number: 5,852,220
[45] Date of Patent: Dec. 22, 1998

[54] PROCESS FOR PREPARING A MIXTURE OF TERTIARY ALKYL ETHERS

[75] Inventors: Harri Järvelin, Helsinki; Petri Lindqvist, Porvoo; Esa Tamminen, Espoo, all of Finland

[73] Assignee: Neste Oy, Espoo, Finland

[21] Appl. No.: 771,417

[22] Filed: Dec. 20, 1996

[30] Foreign Application Priority Data

Dec. 22, 1995 [FI] Finland ..................................... 956254

[51] Int. Cl.$^6$ .................................................. C07C 41/05
[52] U.S. Cl. ............................................................ 568/697
[58] Field of Search ............................................. 568/697

[56] References Cited

U.S. PATENT DOCUMENTS 5,536,886 7/1996 Tamminen et al. ..................... 568/697
5,637,777 6/1997 Aittamma et al. ....................... 568/697

FOREIGN PATENT DOCUMENTS 9203401 3/1992 WIPO .

*Primary Examiner*—Brian M. Burn
*Assistant Examiner*—Sreeni Padmanabhan
*Attorney, Agent, or Firm*—Birch, Stewart, Kolasch & Birch, LLP

[57] ABSTRACT

A process for producing tertiary alkyl ethers by reacting an olefinic hydrocarbon feedstock, which contains a mixture of reactive $C_4$–$C_7$ isoolefins, with an alkanol in the presence of a catalyst that will enhance the reaction between the isoolefins and the alkanol. By adjusting the weight ratio of the isobutylene to the reactive $C_6$ isoolefins of the feed to a value of about 0.2 to 10, it is possible to increase the conversion of reactive $C_4$'s to over 95%, of reactive $C_5$'s to over 85% and of reactive $C_6$'s to over 57%.

13 Claims, 2 Drawing Sheets

PROCESS FOR PREPARING A MIXTURE OF TERTIARY ALKYL ETHERS

BACKGROUND OF THE INVENTION

1. Field of the Invention

The present invention relates to the preparation of tertiary alkyl ether products, which can be used as components of motor fuels. These products contain mixtures of at least two alkyl ethers, in particular methyl t-butyl ether and ethyl t-butyl ether, t-amyl methyl ether or t-amyl ethyl ether, or mixtures thereof, and possibly heavier tertiary alkyl ethers. According to the process, isoolefins, in particular the $C_4$–$C_7$ isoolefins, of an olefinic hydrocarbon feedstock are reacted with a suitable alkanol in the presence of a catalyst in order to prepare the corresponding ethers. These ethers are recovered and, if necessary, they are further processed in order to prepare a motor fuel component.

2. Description of Related Art

Tertiary alkyl ethers are added to gasoline in order to improve the anti-knocking characteristics thereof and to reduce the concentration of harmful components in the exhaust gases. The oxygen-containing ether group of these compounds has been found favourably to improve the combustion process of automotive engines. Suitable alkyl tert-alkyl ethers are methyl t-butyl ether (MTBE), ethyl t-butyl ether (ETBE), t-amyl methyl ether (TAME), t-amyl ethyl ether (TAEE) and t-hexyl methyl ether (THME), to mention a few examples. These ethers are prepared by etherification of isoolefins with monovalent aliphatic alcohols (alkanols). The reactions can be carried out in a fixed bed reactor, in a fluidized bed reactor, in a tubular reactor or in a catalytic distillation column.

The etherification reaction is an exothermic equilibrium reaction, and maximum conversion is determined by the thermodynamic equilibrium of the reaction system. To use TAME as an example, it is possible to obtain an about 90% conversion by carrying out reaction and separation in a reactive distillation column, whereas only a 65 to 70% conversion is obtainable in a fixed bed reactor.

Ion exchange resins are the most common etherification catalysts. Generally the resin used comprises a sulfonated polystyrene/divinyl benzene based cation exchange resin (sulfonated polystyrene cross-linked with divinylbenzene) having particle sizes in the range from 0.1 to 1 mm.

Two TAME processes have been commercially available for some time. The first one comprises fixed bed reactors, columns for product separation by distillation and a methanol separation unit. In the other process, the product distillation is replaced by a catalytic distillation unit, which substantially improves the TAME conversion, as mentioned above.

A third completely novel etherification process is described in our International Patent Application WO 93/19031. This novel process comprises a catalytic distillation unit which has been modified by transferring the catalyst conventionally placed in the distillation column into a separate external reactor which is being fed from the product separation distillation unit. The side reactor product is recycled back to the same product separation distillation unit. According to an embodiment of that process described in our international patent application WO 93/19032, the product distillation of the catalytic distillation reactor system is operated in such a way that most, and preferably practically all, of the alkanol which is removed with the distillate is bound to the inert $C_4$ hydrocarbons of the distillate, forming an azeotrope with them. The product is recovered from the bottom of the column and it comprises a mixture of TAME and heavier ethers.

A suitable feedstock for the above-mentioned processes for preparing tertiary alkyl ethers is Fluidized Catalytic Cracking (FCC) Gasoline containing $C_{4-7}$ hydrocarbons, a substantial portion, generally at least 5%, typically about 7 to 30 wt-%, of which comprises reactive $C_{4-7}$ isoolefins. These reactive isoolefins include the following compounds: isobutene, 2-methyl-1-butene, 2-methyl-2-butene, 2-methyl-1-pentene, 2-methyl-2-pentene, 2,3-dimethyl-1-butene, 2,3-dimethyl-2-butene, 2-ethyl-1-butene, 2-methyl-2-hexene, 2,3-dimethyl-1-pentene, 2,3-dimethyl-2-pentene, 2,4-dimethyl-1-pentene, 2-ethyl-1-pentene and 2-ethyl-2-pentene. Other suitable hydrocarbon feedstocks for etherification processes are formed by Pyrolysis $C_5$ Gasoline, Thermofor Catalytic Cracking (TCC) Gasoline, Residual Catalytic Cracking (RCC) Gasoline and Coker Gasoline.

Although the above-mentioned novel etherification process will provide excellent conversion rates of the reactive $C_5$'s, the conversion of the reactive $C_6$'s to the corresponding tertiary alkyl ethers (e.g., THME, tert-hexyl methyl ether, THEE, tert-hexyl ethyl ether) is less than 50%. Depending on the process configuration and the alkanol used, the conversion of the reactive $C_6$.s can even be less than 40 or 30%. In a mixture containing $C_4$, $C_5$ and $C_6$ -based ethers and the corresponding non-reactive hydrocarbons, an increase of the amount of $C_6$ ethers would significantly reduce the vapor pressure of the ether products, improve the octane number thereof and, considering the fact that the alkanol is a more inexpensive component than the gasoline, increase the cost efficiency of the process.

SUMMARY OF THE INVENTION

The present invention aims at eliminating the problems associated with the prior art by providing a novel process for producing tertiary alkyl ethers from an olefinic hydrocarbon feedstock while increasing the conversion of reactive $C_6$ hydrocarbons and providing high conversion rates of reactive $C_4$ and $C_5$ hydrocarbons.

The present invention is based on the surprising finding that, in the connection with the production of TAME and heavier ethers, the conversion of the $C_6$ hydrocarbons can be enhanced significantly, if the weight ratio of the isobutylene to the reactive $C_6$ isoolefins of the feed is 0.1 to 100, preferably about 0.15 to 10.

Thus, by using a feedstock, which contains olefinic hydrocarbons that subject to an etherification reaction with an alkanol will yield MBTE or ETBE, the conversion of the $C_6$ reactive hydrocarbons, and possibly heavier hydrocarbons present, will increase with some 10 to 30%. The product obtained, which contains a mixture of $C_4$, $C_5$ and $C_6$ based ethers, will have an excellent octane number and good vapor pressure characteristics.

BRIEF DESCRIPTION OF THE DRAWINGS

Next, the invention will be described in more detail with the aid of the attached drawings.

DETAILED DESCRIPTION OF THE INVENTION

Figure 1:
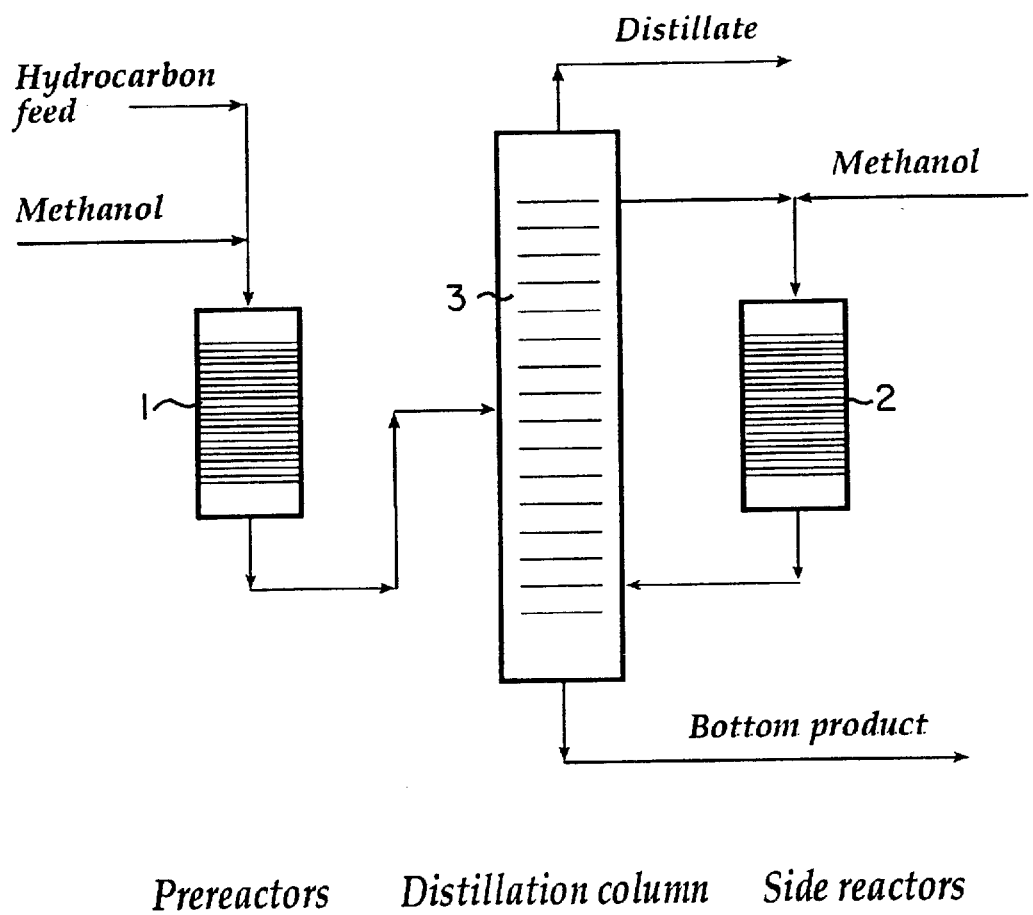
FIG. 1 depicts a simplified process scheme illustrating a basic embodiment of an etherification process according to the present invention, comprising one prereactor, a product separation column and a side reactor, and FIG. 2 gives a schematic, but somewhat more detailed depiction of an etherification unit comprising three prereactors, a product separation column, and two side reactors.

Within the scope of the present application, the expression "catalytic distillation reactor system" denotes an apparatus, wherein the ether product reaction and the separation of the products take place at least partially simultaneously. The apparatus may comprise a conventional reactive distillation column or a distillation column combined with at least one side reactor. Reference is made to the embodiments described in greater detail in International Patent Applications WO 93/19031 and WO 93/19032.

The term "alkanol" includes lower alkyl alcohols capable of forming azeotropes with saturated and unsaturated hydrocarbons, in particular $C_3$ to $C_7$ hydrocarbons, of the hydrocarbon feedstock. As specific examples of the alkanols, the following can be mentioned: methanol, ethanol, n-propanol, i-propanol, n-butanol, i-butanol and t-butanol. Methanol and ethanol are particularly preferred.

The terms "olefinic hydrocarbon feedstock" or "hydrocarbon feedstock" (which are interchangeably used herein), are intended to cover all hydrocarbon feedstocks (conventionally meaning the feed of the prereactors), which contain a mixture of isoolefins which can be etherified to form tertiary alkyl ethers. In particular, the following feedstocks are preferred: $C_4$ fractions from FCC, TCC or RCC, FCC Gasoline, FCC Light Gasoline, Pyrolysis $C_5$ Gasoline, TCC Gasoline, RCC and Coker Gasoline. The feed can also comprise a mixture of two or more olefinic hydrocarbon feedstocks, such as a mixture of a $C_4$ fraction from FCC with FCC Light Gasoline and a pyrolysis $C_5$ cut. The proportion of the various $C_4$ to $C_7$ isoolefins will, of course, to a large extent determine the composition of the ether product.

A particularly preferred hydrocarbon feedstock comprises a mixture of a FCC gasoline fraction, containing $C_4$ to $C_7$ isoolefins, and a liquid gas fraction containing isobutylene.

Of the above feedstocks, FCC, RCC and TCC are preferred because these hydrocarbon cuts can be used as such, possibly after the removal of heavier cuts ($C_{8+}$). The use of Pyrolysis Gasoline requires that the light cut and the $C_{6+}$ cut be removed before it can be fed into the hydrogenation unit. Up to some 10% of the $C_{6+}$ cut can be included in the resulting hydrocarbon mixture, called a Pyrolysis $C_5$ Gasoline, so as to ensure that substantially all of the reactive $C_5$'s of the Pyrolysis Gasoline are present in the olefinic feedstock. This feedstock will also contain reactive aliphatic $C_{6+}$ hydrocarbons. Pyrolysis Gasoline is particularly rich in isoprene (up to 10 wt-%) and other diolefins and the selective hydrogenation will greatly improve the value of this cut as a feedstock for etherification, in particular in combination with any of the above mentioned cracking gasoline cuts.

As mentioned above, the basic concept of the invention is to ensure that the olefinic hydrocarbon feed used for etherification contains at least 10 wt-% isobutylene calculated from the amount of reactive $C_6$ isoolefins of the feed. In particular the weight ratio of the isobutylene to the reactive $C_6$ isoolefins of the feed should be about 0.15 to 10, preferably about 0.2 to 5. As the examples given below will show, the conversion of $C_6$ reactive hydrocarbons (e.g., 2-methyl-1-pentene, 2-methyl-2-pentene, 2,3-dimethyl-1-butene, 2,3-dimethyl-2-butene, 2-ethyl-1-butene) will be increased by over 15% when the weight ratio of isobutylene to reactive $C_6$'s is increased from 0 to 0.25. By using the invention it is surprisingly possible to provide an etherification process, wherein the conversion of the reactive $C_4$'s is over 95%, the conversion of the reactive $C_5$'s is over 85%, and the conversion of the reactive $C_6$'s is over 57%, said conversion rates being calculated from the weight of the components of the olefinic hydrocarbon feedstock.

According to a preferred embodiment, the olefinic hydrocarbon feedstock contains reactive $C_4$, $C_5$ and $C_6$ hydrocarbons in weight ratios of 1:1 to 5:1 to 5.

According to another preferred embodiment, the process according to invention is carried out in a catalytic distillation reactor system, containing a distillation reactor. From the distillation column a bottom fraction is removed, which contains unreacted $C_5$ to $C_7$ hydrocarbons together with tertiary alkyl ethers, and a distillate fraction, which mainly contains butanes and unreacted $C_4$ hydrocarbons and unreacted alkanol. Such a distillate fraction typically contains butane, 1- and 2-butenes and possibly minor amounts of isobutylene. Using methanol as the etherifying alkanol, it will become possible to provide a bottom fraction containing methyl tertiary butyl ether, tertiary amyl methyl ether, and tertiary hexyl methyl ether.

The catalytic distillation reactor system can comprise a distillation column and a side reactor, which is placed in liquid flow connection with the column. Such a process configuration is explained below in connection with the examples. The invention can also be applied to a conventional catalytic distillation reactor. It is operated in the same way as a side reactor process. The only difference is that the alkanol consuming reaction takes place within the column.

Preferably, the catalytic distillation reactor system is provided with a recovery unit for the unreacted alkanol.

The attached drawing gives an overview of a preferred process embodiment according to the present invention. Thus, in such an embodiment an olefinic hydrocarbon feedstock, for instance a mixture of a $C_4$ fraction with FCC Gasoline, optionally after removal of the heavy fraction in an FCC gasoline splitter to produce an FCC Light Gasoline, is conducted to a prereactor unit 1 together with the alkanol, e.g. methanol. In the prereactor the reactants are reacted in the presence of a suitable catalyst to produce a reaction mixture containing $C_4$, $C_5$ and $C_6$ ethers together with unreacted (inert) hydrocarbons. The reaction mixture is conducted to a fractionator 3, i.e. distillation column, in which it is subjected to distillation to provide a bottoms product containing an ether mixture along with the unreacted, inert $C_5$ and heavier hydrocarbons. The distillate contains the unreacted alkanol, and inert $C_4$'s and lighter and, possibly, some unreacted $C_5$'s. A side drawoff is taken from the column 3 and conducted through a side reactor 2. In the reactor 2, the side stream is subjected to further etherification and additional alkanol may, optionally, be fed into the side stream before the side reactor in order to increase the ether yield. The side stream is returned to the distillation column 3 at a point below the feed point of the reaction mixture from the prereactor 1.

Figure 2:
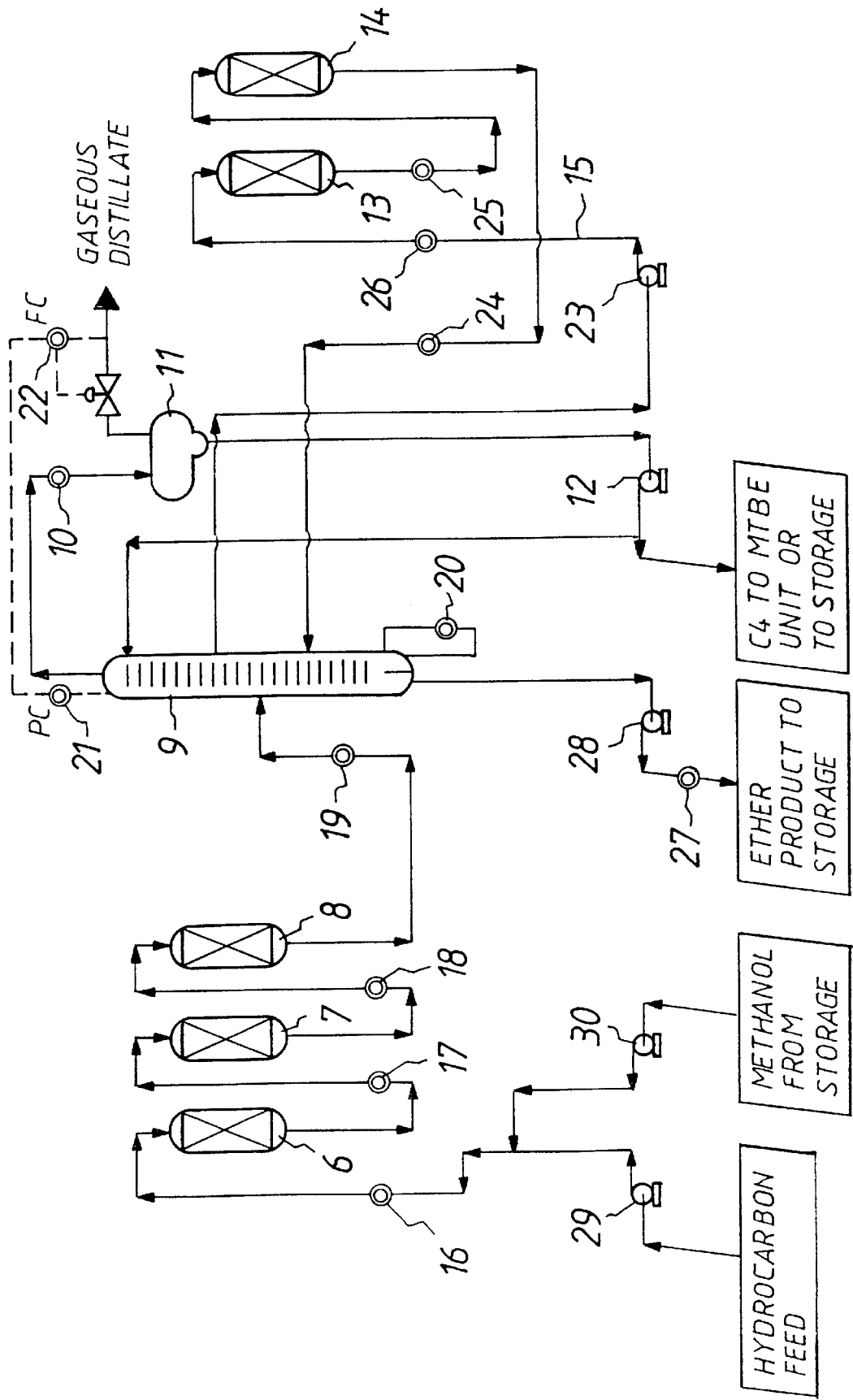

FIG. 2 shows in more detail the configuration of a preferred process embodiment.

Thus, the hydrocarbon feedstock and the methanol needed for the etherification are fed under pressure (pumps 29, 30) and mixed together, the mixture is heated or cooled to obtain a proper feed temperature and then the mixture is fed through prereactors 6, 7 and 8. It should be noticed that, according to the invention, it is possible to feed the alkanol not only into the hydrocarbon feedstock but, in addition, also into the side stream entering the side reactors (cf. below). The prereactors consist of three reactors filled with ion exchange resin. The reactors can be fixed or fluidized bed or tubular reactors. The reactors may be arranged in series, as shown in the figure, or in parallel. If there are more than two prereactors they may also be arranged in series/parallel. Because of the reaction there is a temperature rise in the prereactors in the range from about 5 to about 15° C. depending on the amounts of isoolefins in the feed and on the efficiency of the reactor insulation. Heat-exchangers 16–18 are arranged before the prereactors 6–8 in order to cool or heat the fluid streams to desired temperature.

From the prereactors the mixture is conducted via a further heat-exchanger 19 to distillation column 9, which in the following is also called the main fractionator. The distillation column can be a packed column or one provided with valve, sieve or bubble-cap trays. At the bottom of the column there is fitted a reboiler 20. The overhead of the column is removed via a condenser 10 to a reflux drum 11, from which the overhead is removed by means of a pump 12. A part of the overhead is forwarded to further processing, for instance to alkanol recovery, and a part thereof is returned to the column. MTBE, TAME and heavier ethers are removed with the bottoms product by using a pump 28 and, if desired, cooled 27 before being conducted to storage. In addition to the ethers, the bottoms product also contains unreacted $C_{5+}$ hydrocarbons.

The reflux ratio of the column is preferably from about ½ to 200. Even greater ratios can be used in pilot plant equipments.

Next to the distillation column 9 a side reactor system has been arranged, which consists of two reactors 13, 14 in series. The reactors can, if desired, be replaced by one larger reactor. The side stream flow can be effected as a forced circulation by using a pump or by thermosyphon. Depending on the mode of circulation the reactors can be fixed or fluidized bed reactors or tubular reactors, as mentioned above in the general part of the description. The side reactors are fed with a liquid stream taken from the column. The pressure of the liquid stream can be increased by a pump 23. The side stream is preferably taken from a tray which is located below trays having methanol K-values less than 1. Additional methanol can, if needed, be fed to the side reactor feed before the side reactor (point 15). The reactor feed can be cooled by a heat-exchanger 24 to the reaction temperature before the side reactor. The temperature rises only by a few degrees in the side reactors. The temperature of the liquid stream from the first and the second reactors, respectively, can be adjusted by heat-exchangers 25, 26. From the side reactor system 13, 14 the liquid flow is routed back to column 9. It is then returned to a plate having a methanol K-value greater than 1.

The reactor effluent enters the column typically at a location below the feed coming from the prereactors 6–8. The aim of this arrangement is to make the column 9 operate in such a manner that at least some part of the methanol in the overhead product is bound to the $C_4$ hydrocarbons in the form of an azeotrope.

The distillation is carried out at a pressure generally ranging from about 1.1 to 20 bars, whereas the pressure of the etherification process is about 6 to 40 bars.

When preparing a mixed ether product comprising TAME as the main ether component, the temperature at the top of the distillation column is about 40° to 70° C., typically about 50° to 60° C., and at the bottom of the column about 80° to 150°, typically about 100° to 130° C.

As mentioned above, according to the present invention the distillation column of the reactive distillation unit is operated in such a way that the alkanol is heavier than the hydrocarbons at the top of the distillation column. Therefore, the alkanol not removed from the top will tend to flow downwards within the column. At the same time the vapor-liquid-equilibrium between $C_5$ and heavier hydrocarbons and the alkanol at the bottom of the column is maintained at such a level that the alkanol is lighter than the hydrocarbons. This causes the alkanol to flow upwards from the bottom of the column. Thus, the alkanol will circulate within the distillation system between the top and the bottom of the column. By fitting a reaction bed in the distillation column or by conducting a side stream from the column through a reaction bed in a side reactor, an alkanol consuming reaction can be created which will remove the alkanol from the system.

When operating the process according to the invention, the alkanol concentration of the bottoms product of the column can easily be reduced to as small a value as desired. In the case of methanol, it is possible to reduce its concentration in the bottoms product to below 100 ppm.

The above-described etherification is preferably carried out in the presence of a conventional cation exchange resin. However also different kinds of zeolites can also be used as etherification catalysts. Thus, the resin may contain sulfonic acid groups and it can be obtained by polymerization or copolymerization of aromatic vinyl compounds followed by sulfonation. Examples of aromatic vinyl compounds suitable for preparing polymers of copolymers are: styrene, vinyl toluene, vinyl naphthalene, vinyl ethylbenzene, methyl styrene, vinyl chlorobenzene and vinyl xylene. The acid cation exchange resin typically contain some 1.3 to 1.9 sulfonic acid groups per aromatic nucleus. Preferred resins are based on copolymers of aromatic monovinyl compounds with aromatic polyvinyl compounds, particularly, divinyl compounds, in which the polyvinyl benzene content is from about 1 to 20 wt-% of the copolymer. The ion exchange resin preferably has a granular size of about 0.15 to 1 mm.

In addition to the above resins, perfluorosulfonic acid resins which are copolymers of sulfonyl fluorovinyl ethyl and fluorocarbon can be used.

According to a preferred embodiment the location of the drawoff from the column to the side reactor is selected in such a way that the vapour-liquid equilibrium ratio (the K-value) of the alkanol is smaller than 1 on the (theoretical) trays above it. If TAME is prepared, the process can be operated in such a way that the K-value of the methanol is smaller than 1 on the trays above the drawoff tray. The reaction product containing the alkanol is returned from the side reactor to the column and it is fed to a tray having an alkanol K-value greater than 1. As a result the alkanol gets more enriched in the vapor phase than do the hydrocarbons. The side stream makes up 10 to 95%, typically about from 60 to about 70% of the total liquid flow of the tray above the side drawoff tray. The use of a side reactor is preferred, e.g., for the reasons that the conditions prevailing in the distillation column can be influenced by changing the drawoff location of the side stream and by feeding more alkanol to the reaction bed.

The following examples will illustrate the invention:

EXAMPLE 1

Preparation of methyl ethers

Two mixtures of a $C_4$ fraction and FCC Gasoline, containing different amounts of isobutylene, were etherified with methanol in a process having the configuration shown in FIG. 2. For comparison an FCC Gasoline with only trace amounds of isobutylene (<1,5 wt-%) was also etherified under the same conditions. The compositions of the various streams are indicated in Tables 1, 2 and 3.

TABLE 1

| Component | HC Feed, g/h | Methanol (1), g/h | Methanol (2), g/h | Distillate, g/h | Bottom prod., g/h |
|---|---|---|---|---|---|
| Methanol | — | 7,412 | 300 | 489 | 33 |
| Reactive C4 | 4,468 | — | — | 124 | 3 |
| Inert C4's and lighter | 18,685 | — | — | 17,366 | 1,309 |
| Reactive C5's | 7,219 | — | — | — | 846 |
| Inert C5's | 19,669 | — | — | 40 | 19,630 |
| Reactive C6's | 7,820 | — | — | — | 3,043 |
| Inert C6's | 14,830 | — | — | — | 14,832 |
| C7+'s | 7,500 | — | — | — | 7,540 |
| MTBE | — | — | — | — | 6,822 |
| TAME | — | — | — | — | 9,188 |
| THME | — | — | — | — | 6,596 |
| TAOH | — | — | — | — | 35 |
| Total | 80,191 | 7,412 | 300 | 18,019 | 69,877 |

TABLE 2

| Component | HC Feed, g/h | Methanol (1), g/h | Methanol (2), g/h | Distillate, g/h | Bottom prod., g/h |
|---|---|---|---|---|---|
| Methanol | — | 5,756 | 300 | 255 | 30 |
| Reactive C4 | 2,234 | — | — | 62 | 2 |
| Inert C4's and lighter | 9,342 | — | — | 8,683 | 655 |
| Reactive C5's | 7,219 | — | — | — | 846 |
| Inert C5's | 19,669 | — | — | 30 | 19,630 |
| Reactive C6's | 7,820 | — | — | — | 3,200 |
| Inert C6's | 14,830 | — | — | — | 14,832 |
| C7+'s | 7,500 | — | — | — | 7,540 |
| MTBE | — | — | — | — | 3,411 |
| TAME | — | — | — | — | 9,188 |
| THME | — | — | — | — | 6,272 |
| TAOH | — | — | — | — | 35 |
| Total | 68,615 | 5,756 | 300 | 9,030 | 65,641 |

TABLE 3

Comparative Example

| Component | HC Feed, g/h | Methanol (1), g/h | Methanol (2), g/h | Distillate, g/h | Bottom prod., g/h |
|---|---|---|---|---|---|
| Methanol | — | 4,100 | 300 | 50 | 1 |
| Reactive C4 | — | — | — | — | — |
| Inert C4's and lighter | 870 | — | — | 820 | 50 |
| Reactive C5's | 7,219 | — | — | — | 846 |
| Inert C5's | 19,669 | — | — | 70 | 19,630 |
| Reactive C6's | 7,820 | — | — | — | 3,549 |
| Inert C6's | 14,830 | — | — | — | 14,832 |
| C7+'s | 7,500 | — | — | — | 7,540 |
| MTBE | — | — | — | — | — |
| TAME | — | — | — | — | 9,188 |
| THME | — | — | — | — | 5,655 |
| TAOH | — | — | — | — | 35 |
| Total | 57,908 | 4,100 | 300 | 940 | 61,326 |

Thus, an increase of the isobutylene/$C_6$ reactive ratio from 0 to about 0.6 increased the $C_6$ conversion from 55 to 61%.

EXAMPLE 2

Etherification with ethanol

Example 1 was repeated using ethanol as the etherifying alcohol.

The results obtained are shown in Table 4. The table below that indicates the conversions of the reactive hydrocarbons (for comparison, the normal conversion of $C_6$'s is about 40%).

TABLE 4

| Stream number | 1 | | 2 | | 3 | | 4 | |
|---|---|---|---|---|---|---|---|---|
| Component | kg/h | wt-% | kg/h | wt-% | kg/h | wt-% | kg/h | wt-% |
| Water | 0,00 | 0,00 | 0,02 | 0,50 | 0,00 | 0,00 | 0,00 | 0,00 |
| C4 inerts | 7,56 | 25,21 | 0,00 | 0,00 | 7,41 | 97,28 | 0,15 | 0,59 |
| Isobutene | 2,07 | 6,89 | 0,00 | 0,00 | 0,12 | 1,63 | 0,00 | 0,00 |
| 2-methyl-1-butene | 0,74 | 2,47 | 0,00 | 0,00 | 0,00 | 0,00 | 0,01 | 0,06 |
| 2-methyl-2-butene | 1,60 | 5,34 | 0,00 | 0,00 | 0,00 | 0,00 | 0,45 | 1,76 |
| C5 inerts | 8,71 | 29,03 | 0,00 | 0,00 | 0,02 | 0,29 | 8,69 | 33,69 |
| C6 reactive | 1,91 | 6,36 | 0,00 | 0,00 | 0,00 | 0,00 | 1,01 | 3,92 |
| C6 inerts | 6,90 | 22,99 | 0,00 | 0,00 | 0,00 | 0,00 | 6,90 | 26,74 |
| C7 reactive | 0,00 | 0,00 | 0,00 | 0,00 | 0,00 | 0,00 | 0,00 | 0,00 |
| C7+ hydrocarbons | 0,51 | 1,71 | 0,00 | 0,00 | 0,00 | 0,00 | 0,51 | 1,99 |
| Diethyl ether | 0,00 | 0,00 | 0,00 | 0,00 | 0,00 | 0,102 | 0,00 | 0,00 |
| Ethanol | 0,00 | 0,00 | 3,39 | 99,50 | 0,06 | 0,79 | 0,01 | 0,04 |
| ETBE | 0,00 | 0,00 | 0,00 | 0,00 | 0,00 | 0,00 | 3,54 | 13,72 |
| TAEE | 0,00 | 0,00 | 0,00 | 0,00 | 0,00 | 0,00 | 3,11 | 12,04 |
| THxEE | 0,00 | 0,00 | 0,00 | 0,00 | 0,00 | 0,00 | 1,39 | 5,38 |
| THpEE | 0,00 | 0,00 | 0,00 | 0,00 | 0,00 | 0,00 | 0,00 | 0,00 |
| Tert-amyl alcohol | 0,00 | 0,00 | 0,00 | 0,00 | 0,00 | 0,00 | 0,02 | 0,07 |
| Total | 30,00 | 100,00 | 3,41 | 100,00 | 7,62 | 100,00 | 25,79 | 100,00 |

Stream 1 Hydrocarbon feed, kg/h
Stream 2 Ethanol feed, kg/h
Stream 3 Distillate, kg/h
Stream 4 Bottom product, kg/h The conversions of the reactive hydrocarbons are:
Isobutylene: 94%
Isoamylenes: 80%
Reactive C6: 47%
Reactive C7: 20%.

We claim:

1. A process for producing tertiary alkyl ethers by reacting an olefinic hydrocarbon feedstock, which contains a mixture of reactive $C_4$–$C_7$ isoolefins, with an alkanol in the presence of a catalyst that will enhance the reaction between the isoolefins and the alkanol, wherein the weight ratio of the isobutylene to the reactive $C_6$ isoolefins of the feed is 0.2 to 10.

2. The process according to claim 1, wherein the ratio of the isobutylene to the reactive $C_6$ isoolefins of the feed is 0.2 to 5.

3. The process according any one of claims 1, or 2, wherein the olefinic hydrocarbon feedstock comprises a mixture of a FCC gasoline fraction, containing $C_4$ to $C_7$ isoolefins, and a liquid fraction containing isobutylene.

4. The process according to claim 1, wherein the olefinic hydrocarbon feedstock contains reactive $C_4$, $C_5$ and $C_6$ hydrocarbons in weight ratios of 1:1 to 5:1 to 5.

5. The process according to claim 1, wherein the reaction is carried out in a catalytic distillation reactor system, containing a distillation reactor.

6. The process according to claim 5, which comprises removing from the distillation column a bottom fraction, which contains unreacted $C_5$ to $C_7$ hydrocarbons together with tertiary alkyl ethers, and a distillate fraction, which mainly contains unreacted $C_4$ hydrocarbons and unreacted alkanol.

7. The process according to claim 6, wherein the distillate fraction contains butane, 1- and 2-butenes and at least minor amounts of isobutylene.

8. The process according to claim 6, wherein methanol is used as alkanol and wherein the bottom fraction contains methyl tertiary butyl ether, tertiary amyl methyl ether, and tertiary hexyl methyl ether.

9. The process according to claim 1, wherein, based on the weight of the components of the olefinic hydrocarbon feedstock, the conversion of the reactive $C_4$'s is over 95%, the conversion of the reactive $C_5$'s is over 85%, and the conversion of the reactive $C_6$'s is over 57%.

10. The process according to claim 5, wherein the catalytic distillation reactor system comprises a distillation column and a side reactor, which is placed in liquid flow connection with the column.

11. The process according to claim 5, wherein the catalytic distillation reactor system is provided with a recovery unit for the unreacted alkanol.

12. The process according to claim 1, wherein the catalyst comprises acidic cation exchange resin.

13. The process according to claim 8, wherein the bottom fraction further contains heavier ethers.

* * * * *